US00PP14514P29

(12) United States Plant Patent
Heims

(10) Patent No.: US PP14,514 P2
(45) Date of Patent: Feb. 3, 2004

(54) ***EUPHORBIA AMYGDALOIDES* PLANT NAMED 'GOLDEN GLORY'**

(50) Latin Name: *Euphorbia amygdaloides*
Varietal Denomination: Golden Glory

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/345,815

(22) Filed: Jan. 15, 2003

(51) Int. Cl.[7] ..... A01H 5/00
(52) U.S. Cl. ..... Plt./302
(58) Field of Search ..... Plt./302

*Primary Examiner*—Bruce R. Campell
*Assistant Examiner*—Louanne Krawczewicz Myers
(74) *Attorney, Agent, or Firm*—Klarquist Sparkman, LLP

(57) ABSTRACT

A new and distinct cultivar of *Euphorbia amygdaloides* plant called 'Golden Glory' characterized by very long lasting deep maroon leaves on upright stems flowering in their second year a bright yellow color fading to lime green. 'Golden Glory' has a nice compact habit and is very showy in winter and spring to early summer.

1 Drawing Sheet

Botanical classification: *Euphorbia amygdaloides.*
Variety denomination: 'Golden Glory'.

BACKGROUND OF THE INVENTION

The present invention relates to a new and distinct cultivar of a hardy, suffrutescent perennial, *Euphorbia amygdaloides* 'Purpurea', known by the cultivar name of 'Golden Glory'. The genus Euphorbia is a member of the family Euphorbiaceae.

The new cultivar originated as a chance seedling from a very dark selection of *Euphorbia amygdaloides* 'Purpurea' (seed parent, unpatented). It is most probably self-crossed, but possibly hybridized with a different species. It stood out at the nursery garden with its extremely deep foliage color and clear yellow flowers.

SUMMARY OF THE INVENTION

This new cultivar is characterized by:

1) Long lasting deep purple foliage color. It lasts well past blooming time so the flowers and purple foliage appear together.
2) Deep green foliage in summer and deep purple foliage in winter.
3) Persistent winter foliage of a deep purple.
4) Nice mounding habit, compact and bushy; not spreading rapidly.
5) Bright yellow inflorescences.
6) Bract color past maturity is lime green extending the showiness of the bloom time.
7) Good vigor.
8) Not susceptible to winter wet which causes rot in many Euphorbia species.
9) Excellent mildew resistance.

Asexual propagation by root cuttings as done in Canby, Oreg., shows that the foregoing characteristics and distinctions come true to form and are established and transmitted through succeeding propagations. This new cultivar has been reproduced only by asexual propagation (division and tissue culture). Each of the progeny exhibits identical characteristics to the original plant. The present invention has not been evaluated under all possible environmental conditions. The phenotype may vary with variations in environment without a change in the genotype of the plant.

BRIEF DESCRIPTION OF THE PHOTOGRAPH

The photograph shows a two-year-old plant, in bloom, growing in the ground in a garden in April in Canby, Oreg.

DETAILED PLANT DESCRIPTION

The following is a detailed description of the new cultivar based on observations of two-year-old specimens grown in the garden in Canby, Oreg. The color descriptions are all based on The Royal Horticultural Society Colour Chart.

Botanical name: *Euphorbia amygdaloides.*
Cultivar name: 'Golden Glory'.
Plant:
- *Type.*—Suffrutescent, herbaceous perennial.
- *Form.*—Upright, clumping.
- *Hardiness.*—USDA Zone 6B to 10.
- *Size.*—55 cm tall and 60 cm wide.
- *Habit.*—Mounding, compact and bushy.

Stem:
- *Type.*—Upright, unbranched, tufted stems which are leafy the first year and flowering the second year.
- *Size.*—6 to 8 mm wide and 55 cm tall.
- *Internodes.*—5 to 10 mm.
- *Surface.*—Glabrous.
- *Color.*—Maroon, Greyed Purple 183B.

Leaf:
- *Type.*—Simple.
- *Arrangement.*—Rosette or alternate.
- *Shape.*—Spatulate to obovate.
- *Venation.*—Pinnate.
- *Margins.*—Entire.
- *Apex.*—Acute.
- *Base.*—Attenuate.
- *Blade size.*—6.3 cm long and 1.4 cm wide.
- *Vestiture.*—Sparsely pubescent below and glabrous above.

*Aspect.*—Matte.
*Texture.*—Leathery.
*Petiole length.*—0.7 cm.
*Petole color.*—Greyed Purple 183A.
*Leaf color.*—Spring: Topside — Maroon. The top leaves are Greyed Purple 187A and blacker. They become greener going down the stem, lightening to Green 147A with some maroon near stem. The new growth before flowering is Greyed Purple 187A top and bottom. Bottom side — Blue gray with purple veins (and tips on top leaves), closest to Greyed Green 191A. Summer: Topside — Closest to Green 139A. Bottom side — Closest to Greyed Orange 177A.

Inflorescence:
*Type.*—Terminal cyme.
*Number of involucre branches.*—14 to 24 per cyme, increases with age.
*Involucre basal bracts.*—One at the base of each involucre branch, oblong, entire, clasping with a broadly acute tip on lower branches and obtuse tip on the upper branches. Size ranges from 4 cm long and 1.2 cm wide to 2.5 cm long and 1.7 cm wide.
*Peduncle.*—Height — 35 to 60 cm from old stem. Diameter — 0.4 cm. Texture — Tomentose. Color — Greyed Purple 183B.
*Pedicel.*—Length — 2.5 cm. Texture — Sparsely pubescent. Color — Greyed Purple 183B.
*Bloom period.*—April to June.
*Fragrance.*—None.

Flower bracts involucres (the showy part of the flower):
*Size.*—0.5 to 2.5 cm wide, 1.8 cm deep.
*Number of flower bracts per involucre branch.*—1 to 30.
*Description.*—Orbicular, two lobed, with an entire margin, an obtuse tip, and a clasping base.
*Color.*—Lime green, Yellow Green 144A to yellow when past maturity, Yellow Green 154A.

Cyathia: The same as the species: Cyathia on a pedicel subtended by a bract in a pseudocyme with 1 female and 2 male flowers per cyathia. Pollen is Greyed Orange 163A. Female flower is lime green, Yellow Green 149C.

Fruit:
*Size.*—5 mm wide and 5 mm long.
*Description.*—A 3-celled carpel.
*Color.*—Maroon, Greyed Purple 187C.

Seed: Few.
*Size.*—2 mm wide and 3 mm long.
*Description.*—Ovoid.
*Color.*—Brown 200D.

Disease tolerance: Excellent tolerance to root rots, the common problem of the Euphorbia species. This cultivar has shown excellent resistance to mildew (a common ailment of *E. amygdaloides* 'Purpurea'). This trait suggests that it is the result of a possible cross-fertilization with another unknown seedling with such characteristics.

Comparisons to similar Euphorbia: Compared to its parent, *Euphorbia amygdaloides* 'Purpurea', this new cultivar has even deeper maroon leaf color and longer lasting leaf color. The contrast between the deep maroon of the leaves and the bright yellow of the flower bracts is striking.

I claim:

1. A new and distinct cultivar of *Euphorbia amygdaloides* plant substantially as shown and described.

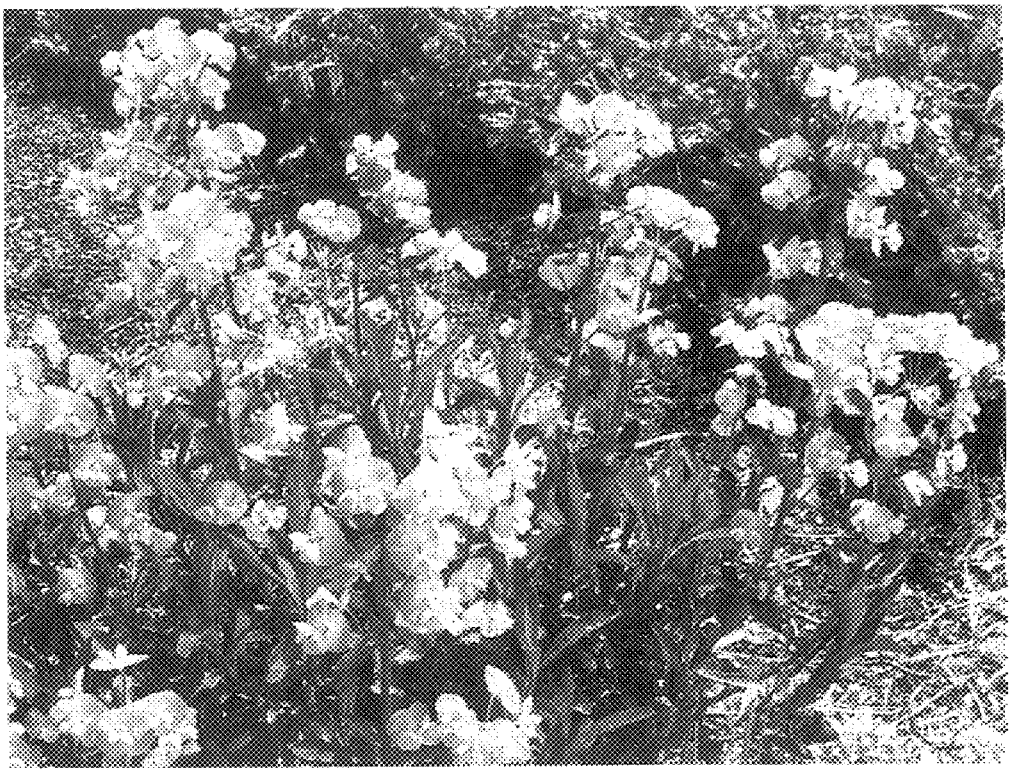

* * * * *